United States Patent [19]
Collis et al.

[11] Patent Number: 5,840,878
[45] Date of Patent: Nov. 24, 1998

[54] VEHICLE FOR DELIVERY OF PARTICLES TO A SAMPLE

[75] Inventors: Matthew P. Collis, Seven Valleys, Pa.; Stephen H. Szczepanik, Catonsville, Md.

[73] Assignee: Becton Dickinson and Company, Franklin Lakes, N.J.

[21] Appl. No.: 911,697

[22] Filed: Aug. 15, 1997

Related U.S. Application Data

[63] Continuation-in-part of Ser. No. 614,230, Mar. 12, 1996, Pat. No. 5,707,860.
[51] Int. Cl.⁶ .............................. C12M 3/00; C07H 21/00
[52] U.S. Cl. .................... 536/25.4; 536/25.41; 436/524; 436/527; 436/177; 435/283.1; 435/287.2; 435/820
[58] Field of Search ...................... 436/523, 525, 436/527, 175, 177; 435/283.1, 287.2, 287.6, 288.1, 820; 536/25.4, 25.41, 25.42

[56] References Cited

U.S. PATENT DOCUMENTS

| | | | |
|---|---|---|---|
| 4,487,700 | 12/1984 | Kanter | 210/789 |
| 5,169,543 | 12/1992 | Shibata | 210/789 |
| 5,374,522 | 12/1994 | Murphy et al. | 435/6 |
| 5,643,767 | 7/1997 | Fischetti et al. | 435/91.3 |

*Primary Examiner*—David A. Redding
*Attorney, Agent, or Firm*—David W. Highet, Esq

[57] ABSTRACT

The present invention relates to a vehicle for delivery of particles to a sample of cells. The vehicle includes a barrier to retain the particles, which barrier is a dissolvable material. Once released into the sample, the particles are useful in methods to lyse or disrupt cells or in methods to separate cellular components from one another if the cells in the sample are already lysed or disrupted.

9 Claims, 4 Drawing Sheets

VEHICLE FOR DELIVERY OF PARTICLES TO A SAMPLE

RELATED APPLICATIONS

This is a continuation-in-part of U.S. patent application Ser. No. 08/614,230, filed Mar. 12, 1996, now U.S. Pat. No. 5,707,860.

BACKGROUND OF THE INVENTION

Access to cellular components such as nucleic acids is imperative to a variety of molecular biology methodologies. Such methodologies include nucleic acid sequencing, direct detection of particular nucleic acid sequences by nucleic acid hybridization and nucleic acid sequence amplification techniques.

Although access to nucleic acids from the cells of some organisms does not involve particularly complex methodologies or harsh treatments, other organisms have cells from which it is particularly difficult to access nucleic acids or other cellular components. Organisms in the latter group include species of the genus Mycobacteria, yeast and fungi. Usually, the difficulty in cellular component access is a result of organism cell walls which are highly resistant to lysis or disruption, and/or the adherence of certain cellular components such as nucleic acids to cellular proteins and other cellular substances such as pieces of cell walls.

Recently, a new method to access nucleic acids has been discovered which is more fully disclosed in a co-pending patent application Ser. No. 08/614,108, filed on Mar. 12, 1996, the 25 disclosure of which is expressly incorporated herein by reference. Briefly this new method to access nucleic acids involves subjecting a sample of disrupted cells to agitation in the presence of particles to separate nucleic acids from other cellular components. This method has been found to be particularly useful to access nucleic acids from the cells of mycobacterial organisms after those cells have been disrupted by the application of heat.

However, the addition of the particles to the sample of cells was found to present certain difficulties. Generally, the particles are scooped from a bulk quantity into the sample, and thus there tend to be inconsistent quantities of particles delivered to the sample. Also, the scooping and attempt to deliver as precise and consistent an amount of particles to the sample adds additional time to the overall process. Furthermore, in the attempt to deliver a precise amount of particles to the sample, the scoop delivering the particles is brought in close proximity to the opening of the sample container, and thus risks contamination of the scoop, and subsequent contamination of the bulk quantity of particles and all further samples to which particles are added. Moreover, occasionally, a particle becomes lodged at the opening of the sample container in such a manner that a proper seal can not be established. This would often result in sample loss, particularly if a heating step is involved in the process.

SUMMARY OF THE INVENTION

The present invention provides solutions to these difficulties encountered when adding particles to samples of cells by providing a vehicle with a barrier to retain the particles until the particles are released into the sample. The barrier may be of any nature which will cause release of the particles for use in agitation of the sample to disrupt cells and/or separate cellular components from one another. One embodiment of the vehicle is a matrix of particles retained by a binding agent which is dissolvable in the sample.

BRIEF DESCRIPTION OF THE DRAWINGS

The various objects, advantages and novel features of the invention will be more readily appreciated from the following detailed description when read in conjunction with the appended figures in which.

DETAILED DESCRIPTION OF THE INVENTION

In a broad aspect, the present invention provides a vehicle for delivering particles to a sample of cells. The vehicle includes a barrier which retains the particles until released into the sample.

Based on the desired objects of the invention, that is to deliver a precise, consistent quantity of uncontaminated particles to a sample of cells, the vehicle may be of a variety of forms. Suitable vehicles include some type of barrier to retain the particles until release into the sample.

For example, vehicles may have physical barriers to retain the particles, and thus take the form of receptacles such as vessels, capsules, sacks, pods, pouches and other containers and carriers. Alternatively, the vehicles may have other physical barriers, which rather than surrounding the particles to retain them, are on the particles such as dissolvable binding agents, for example, dissolvable glues such as trehalose, pastes, mortars or other adhesives. Yet another embodiment is a vehicle for which the barrier is a non-physical means for retaining the particles as a unit prior to release into the sample such as electrostatic forces.

Figure 1:
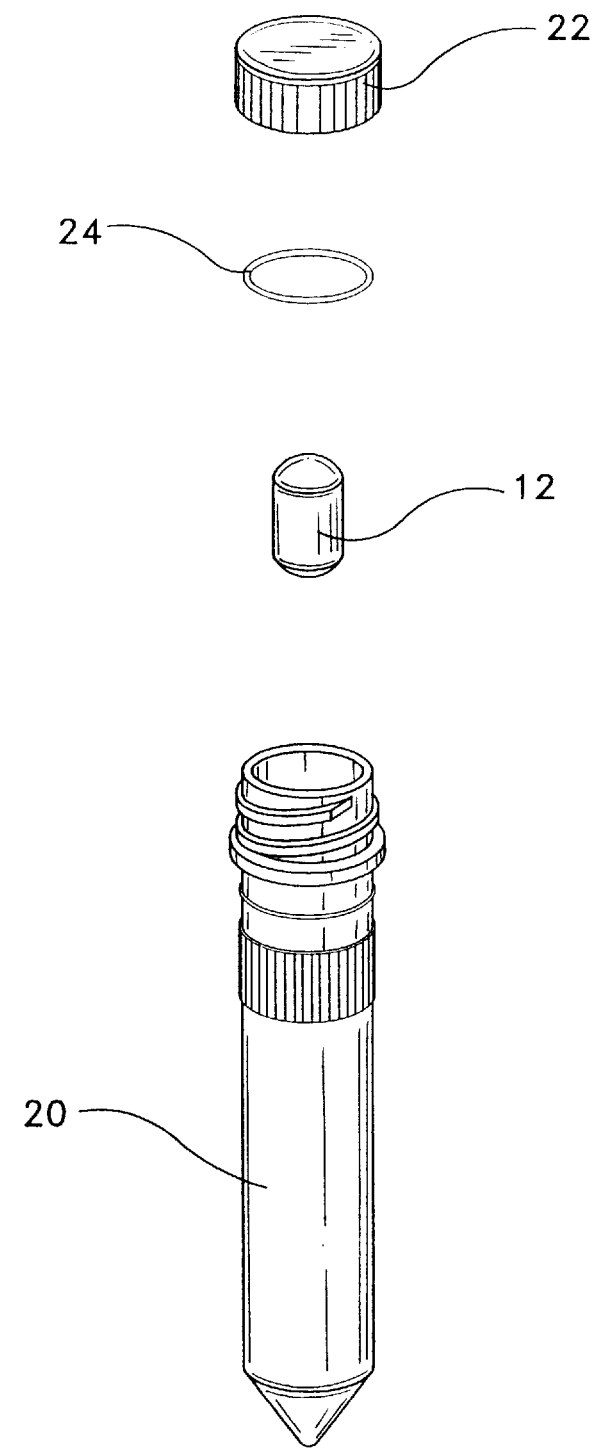
FIG. 1 is an exploded perspective view of one embodiment of the vehicle of the present invention and a typical screw cap sample tube into which the vehicle would be placed.
Figure 2:
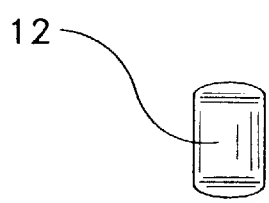
FIG. 2 is an exploded cross-sectional view of the vehicle and sample tube of FIG. 1.
Figure 2:
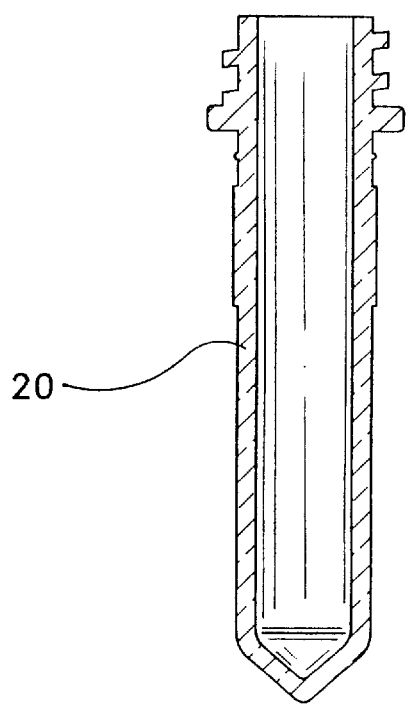
Figure 3:
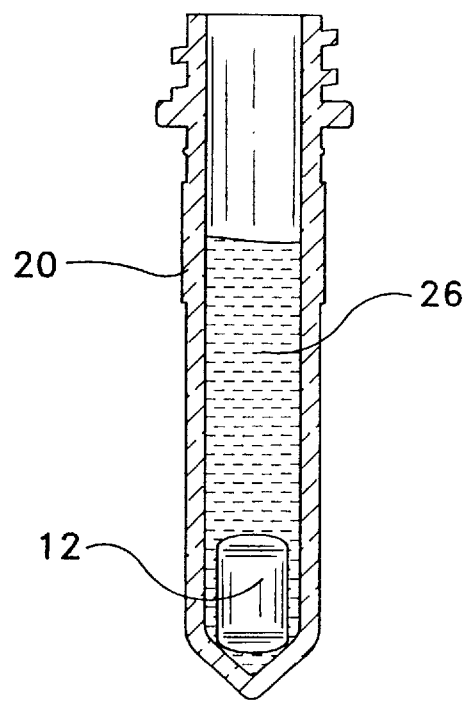
FIG. 3 is a cross-sectional view of the vehicle in a sample in the sample tube.
Figure 4:
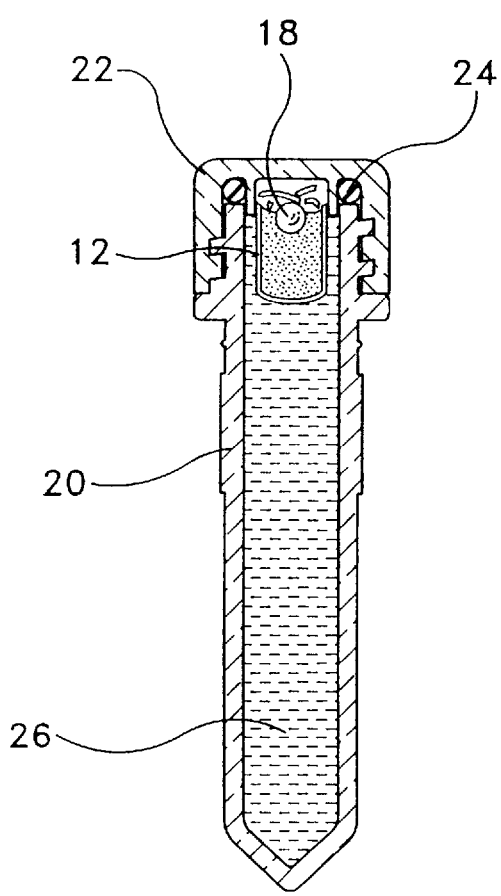
FIGS. 4 and 5 are a cross-sectional view of released particles in the sealed sample tube during agitation.
Figure 5:
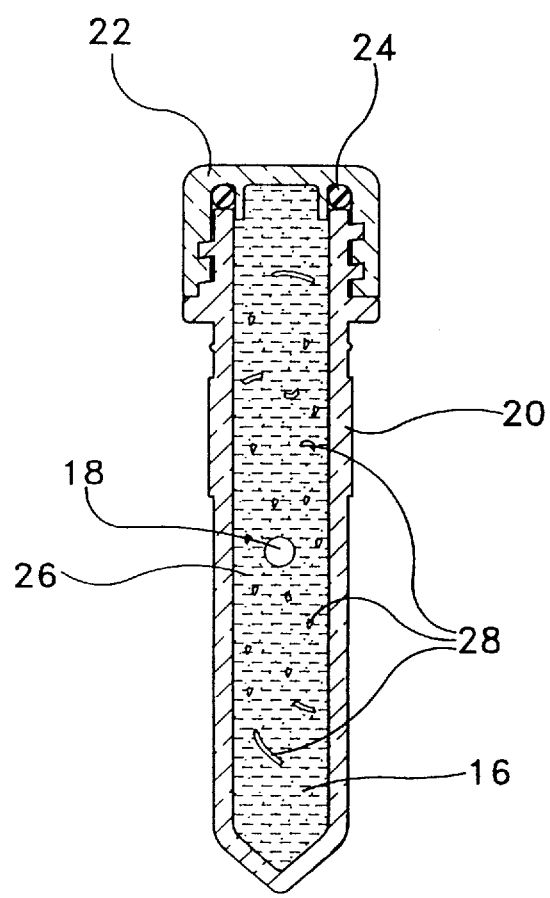
Figure 6:
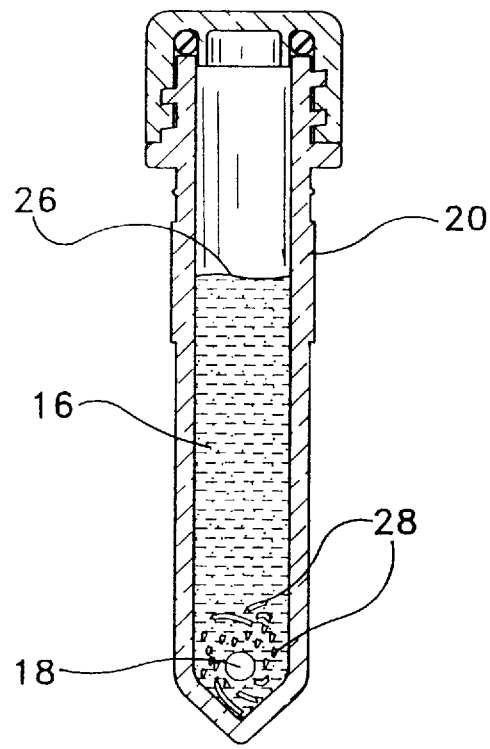
FIG. 6 is a cross-sectional view of released particles in the sealed sample tube after agitation is completed.
Figure 7:
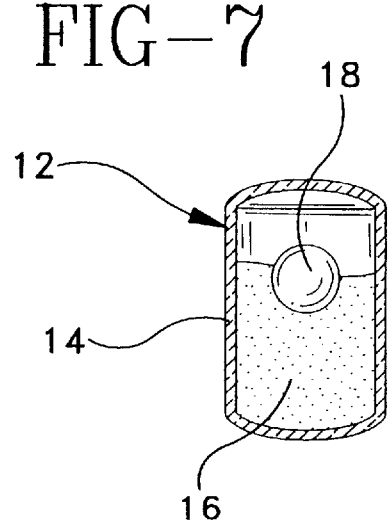
FIG. 7 is an enlarged view of the vehicle.

One example of a suitable vehicle is illustrated in FIG. 7 which shows a matrix 12 of particles 16 and 14 from which the particles are releasable. In this embodiment, the barrier is the dissolvable binding agent 14 of the matrix.

In such an embodiment, the barrier may be made of any material which can be designed to retain the particles 16 until their desired release into a sample. For example, such a barrier may be any dissolvable or meltable material which can retain the particles 16 in a form until their release due to dissolving or melting of the material. Also, a portion of the barrier may be dissolvable or meltable whereas the remainder of the barrier is not so, such that particle release occurs from only a portion of the vehicle.

In the case of a dissolvable barrier material, the material is selected based on the nature of the sample and the desired time of release of the particles. Certain sugar materials, pastes, mortars and other dissolvable adhesives, for example, may generally be customized by inclusion of particular constituents to dissolve at faster or slower rates. One preferred dissolvable binding agent is trehalose.

A solution of trehalose is mixed with pellets to create a slurry. A preferred concentration for the trehalose solution is ten percent, weight to volume. Portions of the slurry are deposited on a surface or into a mold, and allowed to dry to form the vehicle as a matrix of particles and trehalose. Such drying may be accelerated by subjecting the slurry portions to a vacuum. Other useful dissolvable binding agents which will create a matrix with particles may be easily determined by those skilled in the art with a reasonable expectation of success by performing a routine screening assay in which slurries of pellets and solutions of suspected dissolvable binding agents are created, dried, and then added to samples to determined dissolution and release of particles.

Alternatively, matrices of dissolvable binding agent and pellets are created by compressing these two components with a tablet press, for example. As with the matrices created from dried slurries, those skilled in the art will also be able to easily determine useful dissolvable binding agents for compression with pellets with a reasonable expectation of success by performing a routine screening assay. Such a routine screening assay will involve the compression of binding materials with pellets to determine whether an intact matrix is produced, and then determination of the dissolution of the matrix and release of pellets into sample.

With a meltable barrier material, the material need merely be selected based on its melting profile (temperature and time or rate). For example, when used in a sample processing method that includes a heating step to render infectious organisms noninfectious and/or disrupt cells, a barrier material which melts at temperatures greater than about 80° C. is suitable as most such heating steps apply temperatures of at least 80° C. to the sample.

The particles 16 may be of various compositions including for example, glass, plastic, sand silicates, latex, crystals, metals such as zirconium, metal oxides, etc. Due to the use of the particles in an agitation process to disrupt cells or to separate cellular components from one another in a sample of disrupted cells, the particles preferably remain undissolved in the sample for a time sufficient to complete the agitation process. Although non-dissolvable particles are preferred, a particle with a slow rate of dissolution would also be suitable.

The particles may also be of various shapes, including for example, spheres, cubes, oval, capsule-shaped, tablet-shaped, non-descript random shapes, etc., and may be of uniform shape or non-uniform shapes. Whatever the shape of a particle, its diameter at its widest point is generally in the range of from about 0.1 mm to about 0.15 mm. Particles with diameters greater than about 0.5 mm have been found to be not as effective in separating cellular components from one another.

The amount of particles retained in the vehicle is dependent upon the amount of and viscosity of the sample to which the vehicle is added. Generally, a typical clinical sample from which a clinician would desire to access nucleic acids for diagnostic purposes has a volume of about 1 mL or less. However, other samples such as environmental samples or food product samples may have greater volumes, and other samples may have lesser volumes.

The viscosity of different samples may vary. For example, within the category of clinical samples, a sputum sample is generally more viscous than a blood or urine sample. Similarly, the viscosities of different environmental samples will also vary.

As a general rule, in viscous samples such as sputum, the volume of particles added to a given volume of sample will be in a ratio of about 0.25:1 to about 1:1. With less viscous samples, a lesser volume to volume ratio of particles to sample is believed to be sufficient to access nucleic acids from the sample.

The vehicle of the present invention can be used to deliver particles to a sample for a variety of purposes. However, commonly, the vehicle will deliver particles to a sample of cells for a cell disruption or lysis process including agitation or sonication of the sample. Such cell lysis or disruption processes are well known to those skilled in the art from references such as Hurley, S. S. et al., *J. Clin. Microbiol.* 25 (11) 2227–2229 (1987) which describes the agitation of samples of mycobacterial cells with beads and the lysogenic agent, phenol, in a Biospec Mini-Beadbeater instrument and Shah, J. S. et al., *J. Clin. Microbiol.* 33 (2) 322–328 (1995) which describes the agitation of samples of *M. tuberculosis cells* with beads and the lysogenic agent, guanidinium thiocyanate (GuSCN), in a GENE-TRAK Sample Processing instrument.

Another use of the vehicle of the present invention is to deliver particles to a sample of cells which have already been lysed or disrupted. It has been found that agitation of such a sample of disrupted cells with particles provides optimal yields of accessible nucleic acids due to separation or shearing of the nucleic acids from other cellular components such as proteins and cell wall fragments. Such a method for accessing nucleic acids from disrupted cells is taught in greater detail in co-pending U.S. patent application Ser. No. 08/614,108, filed on Mar. 12, 1996, the disclosure of which is expressly incorporated herein by reference.

Samples of cells, whether disrupted or not, are typically contained in a sample tube 20 such as that shown in FIG. 1. In order to avoid loss of sample during agitation or other manipulations, such tubes generally have a screw-cap 22 and a gasket (o-ring) 24 to aid in providing a tight seal between the top of the sample tube and the screw-cap.

As shown in FIG. 2 and FIG. 3, the vehicle 12 is placed into the sample tube 20 either before or after a sample 26 is added. As stated above, the sample 26 may be of intact, non-disrupted cells or of disrupted cells or a combination of both. As shown in FIG. 3, a vehicle 12 with a dissolvable binding agent 14 will generally begin to release particles 16 soon after the vehicle 12 contacts the sample 26. In contrast, a vehicle 12 with a meltable barrier will generally remain intact and not release particles 16 until the temperature of the sample 26 is sufficient to melt the barrier 14.

Once the sample tube 20 has been capped, as shown in FIG. 4, the tube may be agitated which causes the sample 26 and the particles 16 to move throughout the tube. As the particles 16 move through the sample, such particles are distributed throughout the sample 26 as also shown in FIG. 4. Following the completion of agitation of the sample, the particles 16 settle to the bottom of the sample 26 as shown in FIG. 6, thus permitting removal of the sample from the tube by pipetting or other similar means without interference from the particles.

Some of the advantages of a vehicle 12 which is a matrix of dissolvable binding agent 14 and particles 16 are its ease of manufacture, low cost, and easy adjustability for delivery of different amounts of pellets to different volumes of samples or different types of samples. Particularly, in comparison to vehicles with frangible barriers, such is some of those described in U.S. Ser. No. 08/614,230, filed Mar. 12, 1996, vehicles of the present invention are easier to manufacture, present less risk of breakage, and are of lesser volume.

The following examples illustrate specific embodiments of the invention described in this document. As would be apparent to skilled artisans, various changes and modifications are possible and are contemplated within the scope of the invention described.

EXAMPLE 1

Preparation of Vehicles With a Soluble Barrier

This example was performed to show the feasibility of preparing a vehicle with a soluble barrier to deliver particles to a sample.

Materials

The materials used in this example were:
- 50% Trehalose solution
- Zirconium beads (0.1 mm diameter) (BioSpec)
- Reverse Osmosis Deionized (RODI) Water
- Labcraft® 2.0 ml capacity conical bottom microfuge tubes Procedure A 10% trehalose solution was prepared by mixing 12 ml of water with 3 ml of the 50% trehalose solution. A small amount of zirconium silicate beads was added to the 10% trehalose solution to create a slurry. Aliquots of the slurry (~200 ul) were deposited in individual weight boats and allowed to dry. The drying was accelerated by placing the aliquots in a vacuum chamber and subjecting the aliquots to a vacuum of 1.0 Torr for 10 minutes.

The resulting vehicles in the form of a matrix of trehalose and zirconium/silicate beads were inserted into each tube which contained 1.0 ml of water.

Results

The vehicles dissolved to release the zirconium/silicate beads into the water in the sample tube.

Conclusion

Vehicles containing a sufficient volume of particles for delivery to a typical sample volume were producible. In addition, the vehicles dissolved as desired and released the particles.

EXAMPLE 2

Determination of Reproducibility of Vehicles

This example was performed to determine whether relatively uniform vehicles could be made repeatedly.

Materials

The following materials were used in this experiment.
- Trehalose (Pfanstiehl)
- Zirconium beads (0.1 mm) (BioSpec)
- RODI Water
- P200 Pipetman
- Rainin filter tips
- Nunc 8 well strip cap, polyethylene
- Large Polystyrene Weight Boats Procedure Two solutions of trehalose were prepared. A 2.5 gram aliquot of trehalose was mixed with 50 ml RODI Water to yield a 5% solution, and a 5.0 gram aliquot of trehalose was mixed with 50 ml RODI water to yield a 10% solution.

The zirconium beads were loaded into the wells of the strip caps which were in a large weight boat to catch any overflow. Between 30 ul and 32 ul of the 5% trehalose solution was added to 80 wells, and the same amount of the 10% trehalose solution was added to another 80 wells. Both sets of wells were allowed to dry at room temperature overnight.

The 5% and 10% trehalose vehicles were collected from the wells with minimal degradation. For both sets of vehicles, each vehicle weighed approximately 0.2 gram.

Results

With either a 5% or 10% trehalose solution, vehicles in the form of a matrix of trehalose and zirconium beads with a consistent weight of about 0.2 gram were reproducibly made.

EXAMPLE 3

Reproducible Production of Vehicles

This example was performed to evaluate a process for reproducible production of vehicles.

Materials
- Trehalose (Pfanstiehl)
- 0.1 mm Zirconium beads (BioSpec)
- RODI Water
- Paraffin sheets
- ½×2×16 inch Delrin sheet with ¼ inch diameter holes (Delrin tablet form)

Procedure

A 10% solution of trehalose was prepared as in Example 2. A slurry of zirconium beads and the 10% trehalose solution was prepared.

The Deirin tablet form was placed on the paraffin sheet and a P-1000 pipette was used to fill tablet forming holes in the Delrin to a 0.58 gram level. The filled forms were dried at room temperature overnight. The filled forms were then subjected to a vacuum of 0.2 Torr for 3 hours and 40 minutes.

Results

Vehicles in the form of a matrix of trehalose and zirconium beads were easily removed from the forms and had uniform weights and consistencies.

EXAMPLE 4

Delivery of Particles from Vehicle to Samples

This example was performed to evaluate the delivery of particles to a sample with a vehicle of the present invention.

Materials

The materials used in this Example were:
- 0.1 mm free Zirconium beads (Cole Palmer)
- 1.0 cm length glass vehicles with 3.0 mm glass bead
- KPDG
- Negative NALC sediment
- Mtb H37Rv
- Labcraft® tubes
- Pre-amplification buffer
- Pre-decontamination buffer
- Decontamination mix
- Amplification mix
- Mtb Hybridization mix
- Genus Hybridization mix
- Internal Amplification Control (IAC) Hybridization mix
- LumiPhos 530®
- AD
- Stringency wash
- System Fluid
- Vehicles (zirconium bead tablets) from Example 3

Procedure

One glass vehicle containing zirconium beads was added to each of three (3) negative control tubes and nine (9) positive control tubes (*Mycobacterium tuberculosis* sequence IS6110 plasmid). Comparative tubes containing an internal amplification control (IAC) sequence plasmid were run for each negative and positive control tube.

One zirconium bead tablet vehicle was also added to each of three (3) negative control tubes and nine (9) positive control tubes. Comparative tubes containing the IAC sequence plasmid were run for each of these negative and positive control tubes also.

Positive control tubes were created by spiking *M. tuberculosis* particles into negative NALC sediment for a final concentration of 500 particles/0.25 ml. One milliliter of KPDG was added to each tube and the tubes were centrifuged at 12,000 g for 3.0 minutes. The supernatant was decanted from each tube, and 1.0 ml of KPDG was added to each tube. The tubes were centrifuged again at 12,000 for 3.0 minutes, and the supernatant decanted.

All tubes were heated in a forced hot air oven for 30 minutes at 105° C., and then agitated using a BIO 101 Savant FastPrep™ instrument at a setting of 5.0 m/s for 45 seconds.

Strand Displacement Amplification (SDA) and detection procedures described in Example 1 of copending U.S. patent application Ser. No. 08/614,108, filed on Mar. 12, 1996, which is expressly incorporated herein by reference, were performed on all tubes of this Example. More specifically, a 30 µl aliquot of each sample ("undiluted sample") was run directly in an SDA assay with the following reagents under the following conditions:

The 30 ul sample was combined with 5 ul of Pre-Amp Buffer in a 0.5 mL microcentrifuge tube. This sample was heated for 3 minutes in a boiling water bath. To this was added 10 ul of the Decontamination Drydown Mix and an amplicon decontamination reaction was conducted for 50 minutes at 41° C. Amplicon decontamination was conducted using a method well known to those skilled in the art from references such as U.S. Pat. No. 5,035,996, the disclosure of which is expressly incorporated herein by reference. Briefly, during a nucleic acid amplification process, the nucleotide dUTP is substituted for dTTP, and thus all products which are replicated from the target DNA sequence (amplicons) contain dUTP instead of dTTP. Then, prior to a nucleic acid amplification process, the sample is contacted with the enzyme uracil DNA glycosylase (UDG). The UDG cleaves the glycosidic bond between uracil and the sugar deoxyribose when dUTP is incorporated into a DNA molecule. Thus, amplicons from previous nucleic acid amplification processes are rendered non-amplifiable (i.e. are not suitable as templates for replication). Therefore, only true target sequence in the sample will serve as template for nucleic acid amplification.

Following amplicon decontamination, 10 ul of the Amplification Drydown Mix was added and the sample incubated for another 2 hours at 41° C. to permit Strand Displacement Amplification (SDA) process to proceed. SDA is a nucleic acid amplification process well known to those skilled in the art. Briefly, Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occur concurrently in the reaction mix. This is in contrast to the PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/ cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'–3' exonuclease deficient polymerase incorporating an α-thio deoxynucleoside triphosphate (αthio dNTP), 3) nicking of a hemimodified double stranded restriction site, 4) dissociation of the restriction enzyme from the nick site, and 5) extension from the 3' end of the nick by the 5'–3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. 1992. *Proc. Natl. Acad. Sci USA* 89, 392–396, Walker, et al. 1992. *Nucl. Acids Res.* 20, 1691–1696 and in U.S. Pat. No. 5,270,184 (hereby expressly incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as a targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

The SDA reaction originally reported in the publications cited above ("conventional SDA") is typically conducted at a temperature between about 35° C. and 45° C., and is capable of $10^8$-fold amplification of a target sequence in about 2 hours. Recently, SDA has been adapted for higher reaction temperatures (about 45°–65° C. - "thermophilic SDA" or "tSDA"). tSDA is capable of producing $10^9$–$10^{10}$ fold amplification in about 15–30 min. at about 50°–60° C. In addition to increased reaction speed, there is a significant reduction in non-specific background amplification in tSDA as compared to conventional SDA.

Detection of amplified target *M. tuberculosis* complex species sequence (IS6110) was conducted in an assay only format on the BDProbeTec™ instrument in duplicate. This detection system is fully described by C. A. Spargo et al. in *Molec. Cellular Probes* 7:395–404 (1993).

The BDProbeTec™ instrument is an automated system for performing SDA assays. The particular details of embodiments of the BDProbeTec™ instrument which was used to automatically perform the detection of amplified target sequences after SDA assays in this Example are disclosed in U.S. patent application Ser. No. 08/409,821, filed Mar. 24, 1995, the disclosure of which is expressly incorporated herein by reference.

Results

The results of this Example are set forth below in Table 1.

TABLE 1

| GLASS CAPSULE | | | | 10% TREHALOSE TABLET | | | |
|---|---|---|---|---|---|---|---|
| ID | M.tb.C Result | IAC RLUs | M.tb.C RLUs | ID | M.tb.C Result | IAC RLUs | M.tb.C RLUs |
| Negative Control | Negative | 321.6 | 0.1 | Negative Control | Negative | 290.0 | 0.1 |
| | Negative | 283.1 | 0.1 | | Negative | 270.4 | 0.1 |
| | Negative | 313.6 | 0.2 | | Negative | 237.7 | 0.2 |
| | Negative | 285.7 | 0.2 | | Negative | 273.6 | 0.2 |
| | Negative | 240.8 | 0.2 | | Negative | 200.4 | 0.2 |
| | Negative | 224.9 | 0.2 | | Negative | 193.5 | 0.2 |
| | Mean | 278.3 | 0.2 | | Mean | 244.4 | 0.2 |
| | SD | 38.6 | 0.1 | | SD | 40.7 | 0.1 |
| | % CV | 13.9 | 31.0 | | % CV | 16.6 | 31.0 |
| Pos B Control | Positive | 182.7 | 36.5 | Pos B Control | Positive | 242.9 | 315 |
| | Positive | 190.2 | 90.9 | | Positive | 250.5 | 259 |
| | Positive | 217.7 | 194 | | Positive | 213.8 | 324.2 |
| | Positive | 212.4 | 487.2 | | Positive | 197.5 | 340.4 |
| | Positive | 237.9 | 75.8 | | Positive | 222.5 | 321.1 |
| | Positive | 273.6 | 206.4 | | Positive | 206.5 | 71.9 |
| | Positive | 247.5 | 241.1 | | Positive | 179.9 | 21 |
| | Positive | 226.9 | 45 | | Positive | 214.4 | 146.3 |
| | Positive | 240.4 | 110.3 | | Positive | 205.2 | 334.9 |
| | Positive | 216.9 | 92 | | Positive | 257 | 603.9 |
| | Positive | 274.5 | 502.1 | | Positive | 238.1 | 317.2 |
| | Positive | 227.6 | 718 | | Positive | 240 | 592.4 |
| | Positive | 92.8 | 10.1 | | Positive | 223.8 | 718.8 |
| | Positive | 142.1 | 47.9 | | Positive | 268.1 | 432.8 |
| | Positive | 201 | 1.9 | | Positive | 249.3 | 61.6 |
| | Positive | 194.9 | 27.1 | | Positive | 213.2 | 301.8 |
| | Positive | 239.5 | 154.3 | | Positive | 204 | 223.8 |
| | Positive | 217.9 | 176.2 | | Positive | 166.2 | 521.4 |
| | Mean | 213.1 | 178.7 | | Mean | 221.8 | 328.2 |
| | SD | 43.8 | 197.7 | | SD | 27.1 | 192.2 |
| | % CV | 20.5 | 110.6 | | % CV | 12.2 | 58.6 |

Conclusion

There were no visually observed differences (i.e., fluidics, viscosity color, etc.) between the samples processed with glass capsule vehicles containing zirconium beads and the zirconium bead tablet vehicles. It was necessary to vortex the tubes in order to dissolve the zirconium bead tablet vehicles. T-tests indicated no statistical difference in RLUs between the samples processed with glass capsule vehicles and the samples processed with tablet vehicles.

EXAMPLE 5

Further Evaluation of Delivery of Particles from Vehicle to Sample

This example was performed to further evaluate the delivery of particles to a sample with a vehicle of the present invention.

Materials

The materials used in this Example were the same as those used in Example 4.

Procedure

The procedure for this Example was substantially the same as that for Example 4, except that tSDA was utilized as described in Example 4 and vehicles and volumes of sample were as follows:

| VEHICLE | VOLUME OF POSITIVE CONTROL SAMPLE | # OF TUBES (# REPS PER TUBE) |
|---|---|---|
| Tablet | 1 ml | 3 (4) |
| Tablet | 0.4 ml | 6 (2) |
| Glass Capsule | 0.4 ml | 6 (2) |

Also, two negative control tubes were processed for each vehicle/positive control sample run described above. These negative controls were run in duplicate, and an IAC sample was run for each negative and positive control tube.

Results

The results of this Example are set forth below in Table 2.

TABLE 2

| | 1 mL with 1 tablet | | | 0.4 mL with 1 tablet | | | 0.4 mL with 1 capsule | | |
|---|---|---|---|---|---|---|---|---|---|
| | MTB | IAC | | MTB | IAC | | MTB | IAC | |
| Negativ | 0.98 | 169.16 | B | Negativ 0.96 | 355.57 | | Negativ 0.94 | 37.95 | |
| | 0.77 | 664.8 | | 0.49 | 273.42 | B | 0.63 | 147.99 | B |
| | 0.99 | 514.02 | B | 0.65 | 472.93 | B | 0.63 | 13.06 | |
| | 0.64 | 471.73 | | 0.74 | 400.96 | | 0.68 | 24.15 | |
| Mean | 0.8 | 454.9 | | Mean 0.7 | 375.7 | | Mean 0.7 | 55.8 | |
| SD | 0.1 | 179.9 | | SD 0.2 | 72.4 | | SD 0.1 | 54.0 | |
| % CV | 17.4 | 39.5 | | % CV 23.9 | 19.3 | | % CV 17.9 | 96.7 | |
| 25 K10 | 1011.32 | 549.04 | B | 25 K10 744.7 | 520 | | 25 K10 3.82 | 95.46 | B |
| | 460.48 | 727.07 | | 329.81 | 288.17 | B | 9.64 | 19.86 | |
| | 48.56 | 132.18 | | 1.44 | 196.64 | | 29.99 | 24.33 | |
| | 70.98 | 436.94 | B | 826.66 | 419.91 | B | 33.93 | 20.57 | B |
| | 39.55 | 403.86 | B | 106.29 | 367.04 | | 1.99 | 34.39 | |
| | 250.64 | 555.36 | B | 0.65 | 96.62 | SS | 83.43 | 271.05 | |
| | 557.05 | 219.83 | | 98.99 | 694.3 | | 21.63 | 38.04 | B |
| | 1033.29 | 283.97 | | 1370.26 | 372.07 | B | 373.72 | 89.16 | |
| | 161.59 | 98.24 | | 3.37 | 63.1 | | 1037.07 | 49.11 | |
| | 8.66 | 119.08 | | 60.09 | 290.91 | B | 43.38 | 444.96 | B |
| | 9.23 | 260.87 | | 105 | 156 | | 0.7 | 26.33 | |
| | 17.44 | 38.97 | | 5.05 | 325.64 | B | 38.95 | 76.93 | B |
| Mean | 305.7 | 318.8 | | Mean 304.4 | 315.9 | | Mean 139.9 | 99.2 | |
| SD | 380.1 | 215.9 | | SD 441.9 | 179.6 | | SD 300.5 | 129.2 | |
| % CV | 124.3 | 67.7 | | % CV 145.2 | 56.9 | | % CV 214.9 | 130.2 | |
| Median | 116.3 | 272.4 | | Median 102.0 | 308.3 | | Median 32.0 | 43.6 | |

B = Bubble in bolus during amp
SS = <10 uL of sample to TB assay

Conclusion

There were no visually observed differences (i.e., fluidics, viscosity, color, etc.) between the processed samples. It was necessary to vortex the tubes in order to dissolve the zirconium bead tablet vehicles. The vehicles of the present invention are a useful means for delivery of particles to a sample which will be subjected to a molecular biological process.

EXAMPLE 6

Comparison of Samples Processed with Glass Capsule Vehicles Containing Zirconium Particles and Samples Processed with Zirconium Particle Tablet Vehicles This example was performed to evaluate whether there are differences between supernatants of samples processed with glass capsule vehicles containing zirconium particles ("Capsules") and the supernatants of samples processed with zirconium particle tablet vehicles ("Tablets").

Materials

The materials used in this Example were:

0.3 gram zirconium particle/trehalose Tablets
100 μL zirconium particle Capsules with 3 mm glass balls
Sample diluent for *M. tuberculosis* complex assay
2 ml sample processing tubes Procedure One Capsule was added to each of five (5) sample processing tubes using a clean disposable forceps. One Tablet was added to each of five (5) sample processing tubes using a clean disposable forceps.

All sample processing tubes were resuspended with 400 μL of the sample diluent. Each tube was processed in a BO 101 Savant FASTPREP™ instrument for 45 seconds at a setting of 5 m/sec$^2$. Following processsing, the supernatants were observed for clarity by transferring 100 μL of the supernatant from each tube onto a microscope slide, and examining the slide at a 10 xpower.

Observations/Results

The supernatants of the samples processed with the Tablets was consistently clear for all five (5) tubes. In contrast, the supernatants of the samples processed with the Capsules was cloudy for all five (5) tubes. The microscopic examination revealed splinter-like debris in the supernatants of the samples processed with the Capsules, whereas no such debris was seen in the supernatants of the samples processed with the Tablets.

Conclusions

The splinter-like debris observed in the supernatants of the samples processed with the Capsules may contribute to undesired interactions or reactions in subsequent processes to which samples may be subjected, such as hybridization or amplification. Therefore, the use of Tablets in processing samples may be a preferred due to the lack of such potentially detrimental debris.

EXAMPLE 7

Comparison of Processing of *M. tuberculosis* Positive Control Samples with Capsules and Tablets This example was performed to compare *M. tuberculosis* positive control samples which are processed with the Capsules to such positive control samples processed with the Tablets.

Materials

The materials used in this Example were:

- 0.3 gram zirconium particle/trehalose Tablets as in Example 6
- 100 $\mu$L zirconium particle Capsules with 3 mm glass balls as in Example 6
- Sample diluent for *M. tuberculosis* complex assay as in Example 6
- 2 ml sample processing tubes containing either *M. tuberculosis* positive control sample or *M. tuberculosis* negative control sample Procedure Forty-four (44) *M. tuberculosis* positive control sample tubes were prepared (#1–44). Using clean disposable forceps, a Tablet was added to each of tubes #1–22. Using clean disposable forceps, a Capsule was added to each of tubes #23–33. Neither a Tablet nor a Capsule was added to tubes #34–44.

All tubes were resuspended with 400 $\mu$L of the sample diluent. Each tube was processed in a BIO 101 Savant FASTPREP™ instrument for 45 seconds at a setting of 5 m/sec$^2$. Tubes #1–11 were subjected to a quickspin (i.e. 15,500 Relative Centrifugal Force in 30 seconds) prior to further processing. Then all tubes were subjected to a tSDA process and a detection process as in Example 4.

Results

The results of this Example are set forth below in Table 3.

TABLE 3

| Tablet with Quickspin | | Tablet without Quickspin | |
|---|---|---|---|
| M. tb RLU | IAC RLU | M. tb RLU | IAC RLU |
| 1267 | 368 | 1429 | 546 |
| 1443 | 521 | 1440 | 448 |
| 1364 | 467 | 1227 | 582 |
| 1531 | 584 | 1000 | 472 |
| 1582 | 542 | 1064 | 611 |
| 1405 | 380 | 1421 | 487 |
| 1485 | 359 | 1273 | 661 |
| 1493 | 489 | 771 | 328 |
| 1349 | 709 | 1238 | 352 |
| 914 | 547 | 1027 | 554 |
| Insufficient Blowback | Insufficient Blowback | 1278 | 641 |
| Mean 1383 | 497 | 1197 | 517 |
| Capsule without Quickspin | | No Tablet, Capsule or Quickspin | |
| M. tb RLU | IAC RLU | M. tb RLU | IAC RLU |
| 48 | 183 | 854 | 257 |
| 1153 | 107 | 29 | 310 |
| 959 | 108 | 555 | 280 |
| 867 | 143 | 975 | 165 |
| 243 | 56 | 1332 | 422 |
| 1 | 139 | 1261 | 360 |
| 208 | 124 | 1060 | 325 |
| 800 | 171 | 65 | 277 |
| 179 | 95 | 564 | 135 |
| 521 | 40 | 1201 | 247 |
| 142 | 197 | Insufficient Blowback | Insufficient Blowback |
| Mean 465 | 124 | 790 | 278 |

TABLE 3-continued

| | M. tb RLU | IAC RLU |
|---|---|---|
| Negative Control | 0.4 | 446 |
| Positive Control | 253 | 126 |

Conclusions

The mean RLUs for both *M. tuberculosis* (M. tb) and Internal Amplification Control (IAC) were higher for the Tablets compared to other conditions. There did not seem to be a need for the quickspin processing with Tablets in the samples used in this Example.

While invention has been described with some specificity, modifications apparent to those with ordinary skill in the art may be made without departing from the scope of the invention. Various features of the invention are set forth in the following claims.

That which is claimed is:

1. A vehicle for delivery of particles to a sample containing cells comprising a dissolvable material which retains the particles until said particles are released into the sample, said particles being sufficiently non-dissolvable to remain undissolved in the sample for a time sufficient to disrupt the cells and render accessible nucleic acids therefrom when the sample is agitated or sonicated.

2. The vehicle of claim 1 wherein the dissolvable material is trehalose.

3. The vehicle of claim 2 wherein the particles and trehalose form a matrix wherein the particles are held in proximity to one another by the trehalose.

4. The vehicle of claim 3 wherein the matrix forms a tablet.

5. The vehicle of claim 1 wherein the particles are glass beads.

6. The vehicle of claim 1 wherein the particles are zirconium/silicate beads.

7. A method for rendering cellular components accessible comprising the steps of (a) adding to a sample containing cells, the vehicle of claim 1;

(b) disrupting the cells to cause release of cellular components;

(c) causing the particles to be released from the vehicle; and (d) agitating the sample sufficiently such that nucleic acids are separated from other cellular components.

8. The method of claim 7 wherein the cells are disrupted by heating the sample at a temperature and for a time sufficient to render infectious organisms in the sample noninfectious.

9. The method of claim 7 wherein the particles are caused to be released from the vehicle by dissolution of the barrier in the sample.

* * * * *